US00PP37055P3

(12) United States Plant Patent
Deng

(10) Patent No.: US PP37,055 P3
(45) Date of Patent: Oct. 21, 2025

(54) ***CALADIUM* PLANT NAMED 'UF-15-30'**

(50) Latin Name: ***Caladium* x hortulanum**
Varietal Denomination: UF-15-30

(71) Applicant: Florida Foundation Seed Producers, Inc., Marianna, FL (US)

(72) Inventor: Zhanao Deng, Riverview, FL (US)

(73) Assignee: Florida Foundation Seed, Producers. Inc., Marianna, FL (US)

( * ) Notice: Subject to any disclaimer, the term of this patent is extended or adjusted under 35 U.S.C. 154(b) by 0 days.

(21) Appl. No.: 19/032,693

(22) Filed: Jan. 21, 2025

(65) Prior Publication Data

US 2025/0241215 P1 Jul. 24, 2025

Related U.S. Application Data

(60) Provisional application No. 63/623,981, filed on Jan. 23, 2024.

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
See application file for complete search history.

(56) References Cited

PUBLICATIONS https://journals.ashs.org/hortsci/view/journals/hortsci/59/2/article-p225.xml (published online Jan. 16, 2024)(retrieved online May 9, 2025) (Year: 2024).*

* cited by examiner

*Primary Examiner* — Susan Mccormick Ewoldt
*Assistant Examiner* — Zachariah Allan Kay
(74) *Attorney, Agent, or Firm* — James R. Holm

(57) ABSTRACT

A new and distinct cultivar of *Caladium* plant named 'UF-15-30', characterized by its compact, dense growth habit; numerous heart-shaped, undulate leaves that have a red purple center, red purple midrib, red purple primary veins, and a green margin; strong tolerance to sunburns; and absence of inflorescence or bloom production.

5 Drawing Sheets

CROSS-REFERENCE TO RELATED APPLICATIONS

This Application is related to and claims the benefit of U.S. Provisional Patent Application Ser. No. 63/623,981 filed on Jan. 23, 2024, entitled *CALADIUM* CULTIVARS, the entirety of which is incorporated herein by reference.

Genus and species: *Caladium* x *hortulanum.*

Cultivar denomination: 'UF-15-30'.

BACKGROUND OF THE NEW CULTIVAR

The present invention relates to a new and distinct cultivar of *Caladium*, botanically known as *Caladium* x *hortulanum*, and hereinafter referred to by the name 'UF-15-30'. *Caladium* plants are tuberous-rooted plants and typically have attractive heart-shaped or arrow-shaped leaves on long stalks rising directly from the tubers. Foliage may grow in a variety of colors and variegation patterns, and many species have been developed for aesthetic coloration, good container and landscape growth, drought tolerance, pest resistance, and other desirable characteristics.

Plant Breeder's Rights for this cultivar have not been applied for.

SUMMARY OF THE INVENTION

The new *Caladium* cultivar 'UF-15-30' has not been observed under all possible environmental conditions. The phenotype of the new cultivar may vary with variations in environment and cultural practices such as temperature, light intensity, fertilization, irrigation, and application of plant growth regulators without any change in genotype.

The objective of the breeding program that produced the present cultivar was to develop cultivars that have novel foliar characteristics, produce multiple brightly colored leaves, have good tuber yield potential, and perform well in containers and the landscape. The present *Caladium* cultivar originated from a cross-pollination made in July 2012 in Wimauma, Florida between the *Caladium* x *hortulanum* cultivar 'Florida Sweetheart' (expired U.S. Plant Pat. No. 8,526), as the female or seed parent, and the *Caladium* x *hortulanum* cultivar 'UF 67' (unpatented), as the male or pollen parent. The new *Caladium* cultivar was discovered and selected by the inventor as a single plant within the progeny of the stated cross-pollination in Wimauma, Florida in September 2014.

Asexual reproduction of the new cultivar 'UF-15-30' by tuber divisions has been performed annually since April 2015. The unique features of this new *Caladium* cultivar are stable and reproduced true to type in successive generations of asexual reproduction.

The new cultivar 'UF-15-30' has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-15-30'. These characteristics in combination distinguish 'UF-15-30' as a new and distinct cultivar of *Caladium:*

1. Compact and dense growth habit;
2. Numerous lance or strap shaped leaves that each have a large red-purple center and multiple red-purple veins radiating from a central main vein of red-purple and connecting with a thin red-purple vein that parallels with the green leaf margins;
3. Strong tolerance to sunburn;
4. Good to excellent leaf health when grown in open fields, containers, and gardens; and
6. Does not produce inflorescences or blooms.

Plant of the new *Caladium* cultivar 'UF-15-30' differ from plants of the female parent, 'Florida Sweetheart', in the following characteristics:

1. Plants of 'UF-15-30' are more tolerant to sunburns in open fields than plants of 'Florida Sweetheart';
2. Leaves of 'UF-15-30' have a large red-purple center and red-purple veins, whereas leaves of 'Florida Sweetheart' have a light rose center and dark rose veins; and
3. Petioles of 'UF-15-30' are thicker and sturdier than the petioles of 'Florida Sweetheart'.

Plants of the new *Caladium* cultivar 'UF-15-30' differ from plants of the male parent, 'UF 67', in the following characteristics:

1. Plants of 'UF-15-30' are much shorter and more compact than plants of 'UF-67';
2. Leaves of 'UF-15-30' are of the lance or strap type with a cordate base, a slightly undulate margin, an acuminate apex, and a pinnate venation pattern, whereas leaves of 'UF-67' are peltate with a palmate-pinnate venation and sagittate to cordate base; and
3. Petioles of 'UF-15-30' are attached at the base of leaves, whereas the petioles of 'UF-67' are attached at the back of the leaves.

Plants of the new *Caladium* 'UF-15-30' can also be compared to plants of the commercial cultivar 'UF 44-4' (U.S. Plant Pat. No. 24,680). Plants of 'UF-15-30' differ primarily from plants of 'UF 44-4' in plant height, leaf color, petiole color and petiole strength. Plants of 'UF 44-4' are shorter and more compact; leaves 'UF 44-4' have a large bright red center extending to the margin; leaves 'UF 44-4' are more undulate; and petioles of 'UF 44-4' are greyed-red at the proximal end.

Plants of 'UF-15-30' can also be compared to plants of the commercial cultivar 'Florida Red Ruffles' (expired U.S. Plant Pat. No. 13,136). Plants of 'UF-15-30' differ primarily from plants of 'Florida Red Ruffles' in leaf color and leaf shape. Leaves of 'Florida Red Ruffles' are more elongated and more undulate and have a red to dark red center extending from the base to the tip.

DESCRIPTION OF THE FIGURES

The accompanying photographs (as shown in FIGS. 1-5) illustrate the overall appearance of the new *Caladium* cultivar 'UF-15-30'. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
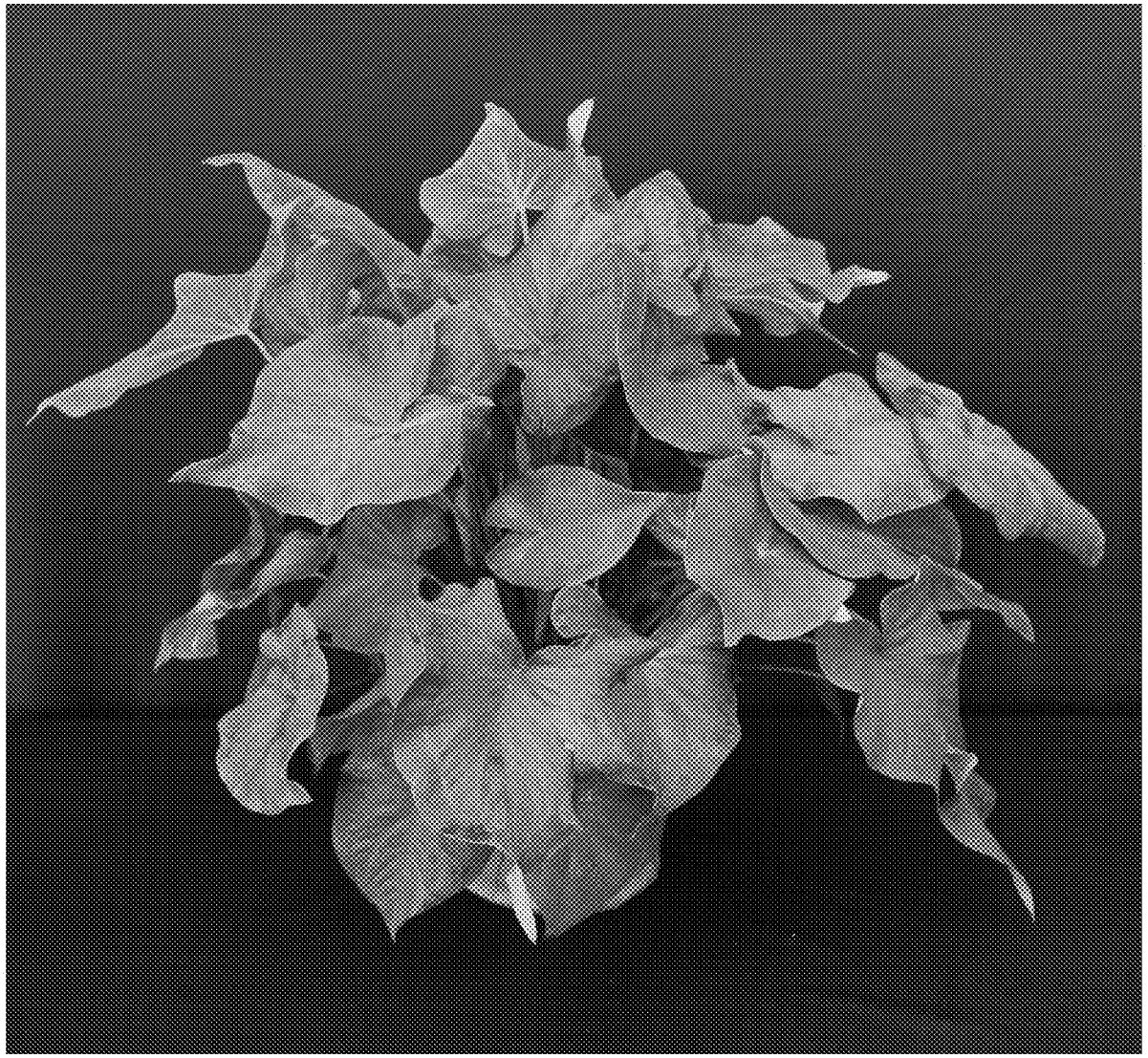
FIG. 1 shows a side perspective view of a typical plant of 'UF-15-30' grown in a container in a greenhouse.
Figure 2:
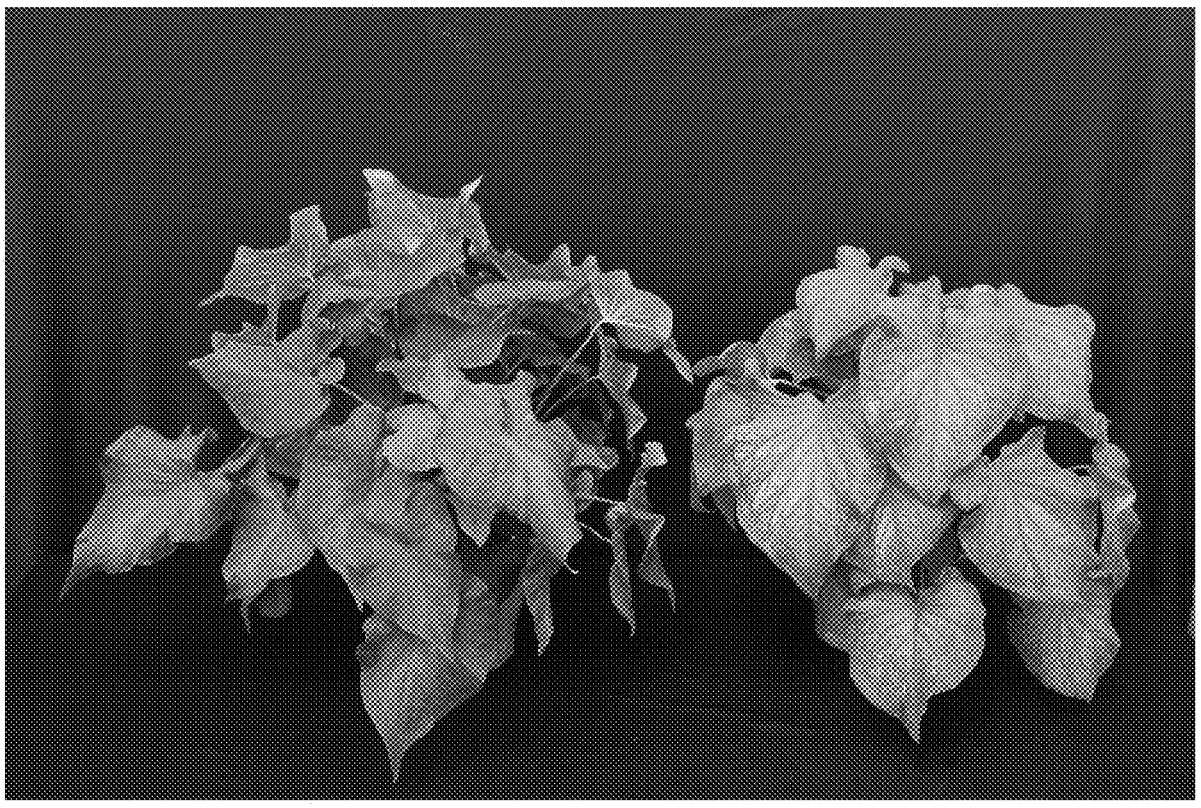
FIG. 2 shows a side perspective view of typical plants of 'UF-15-30' (left) and its seed parent 'Florida Sweetheart' (right) grown in a container in a greenhouse.
Figure 3:
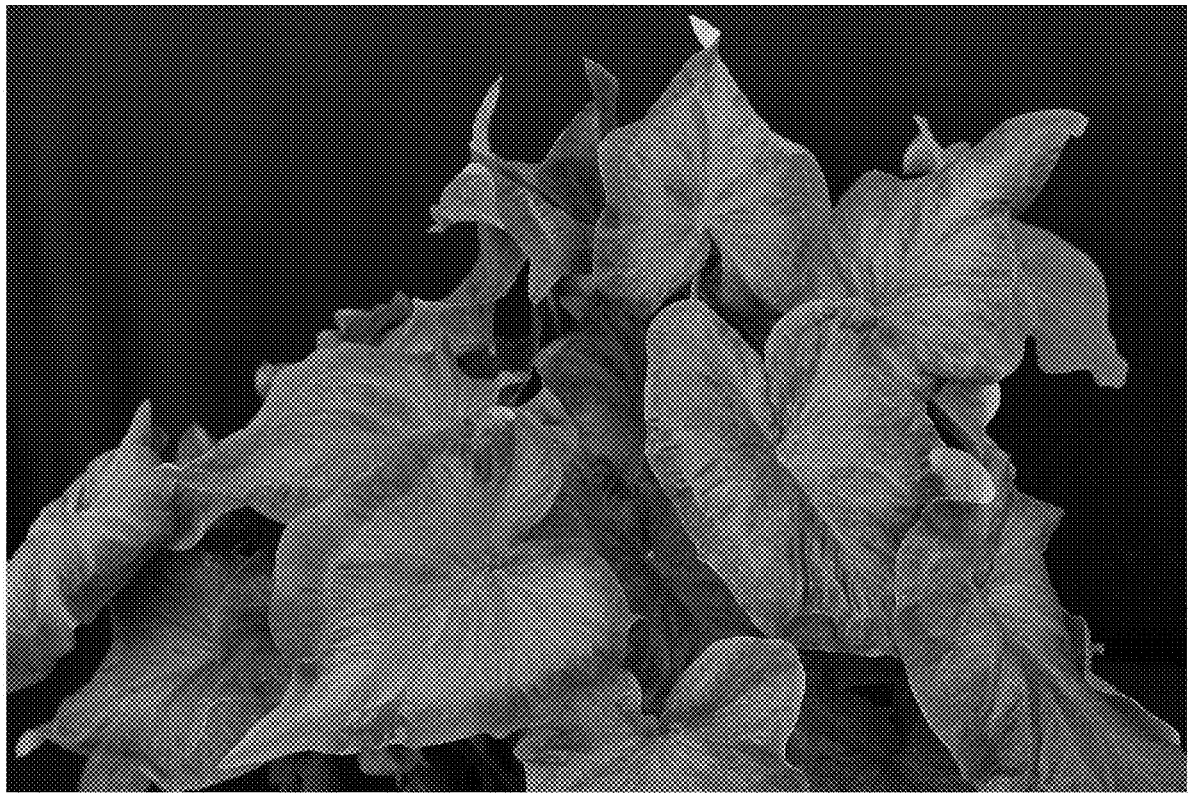
FIG. 3 shows a close-up view of typical leaves of 'UF-15-30' grown in a container in a greenhouse.
Figure 4:
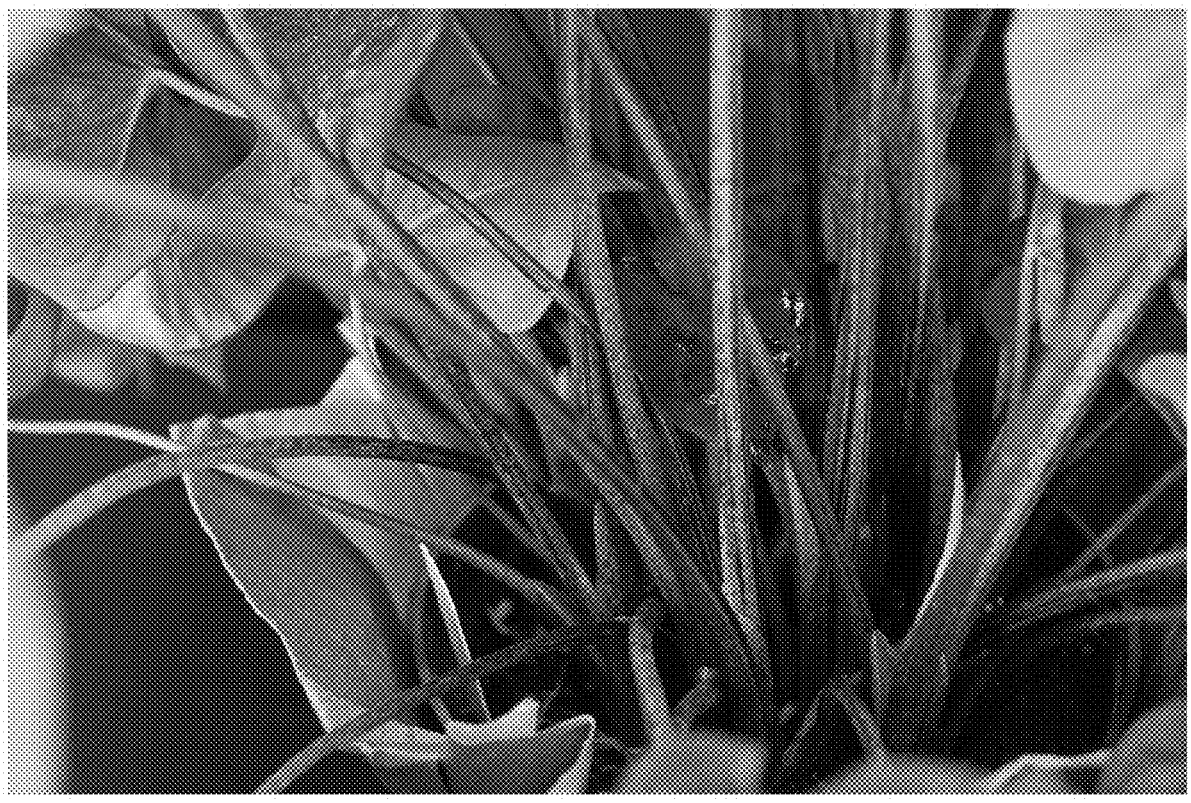
FIG. 4 shows a side perspective view of typical petioles of plants of 'UF-15-30' grown in a greenhouse.
Figure 5:
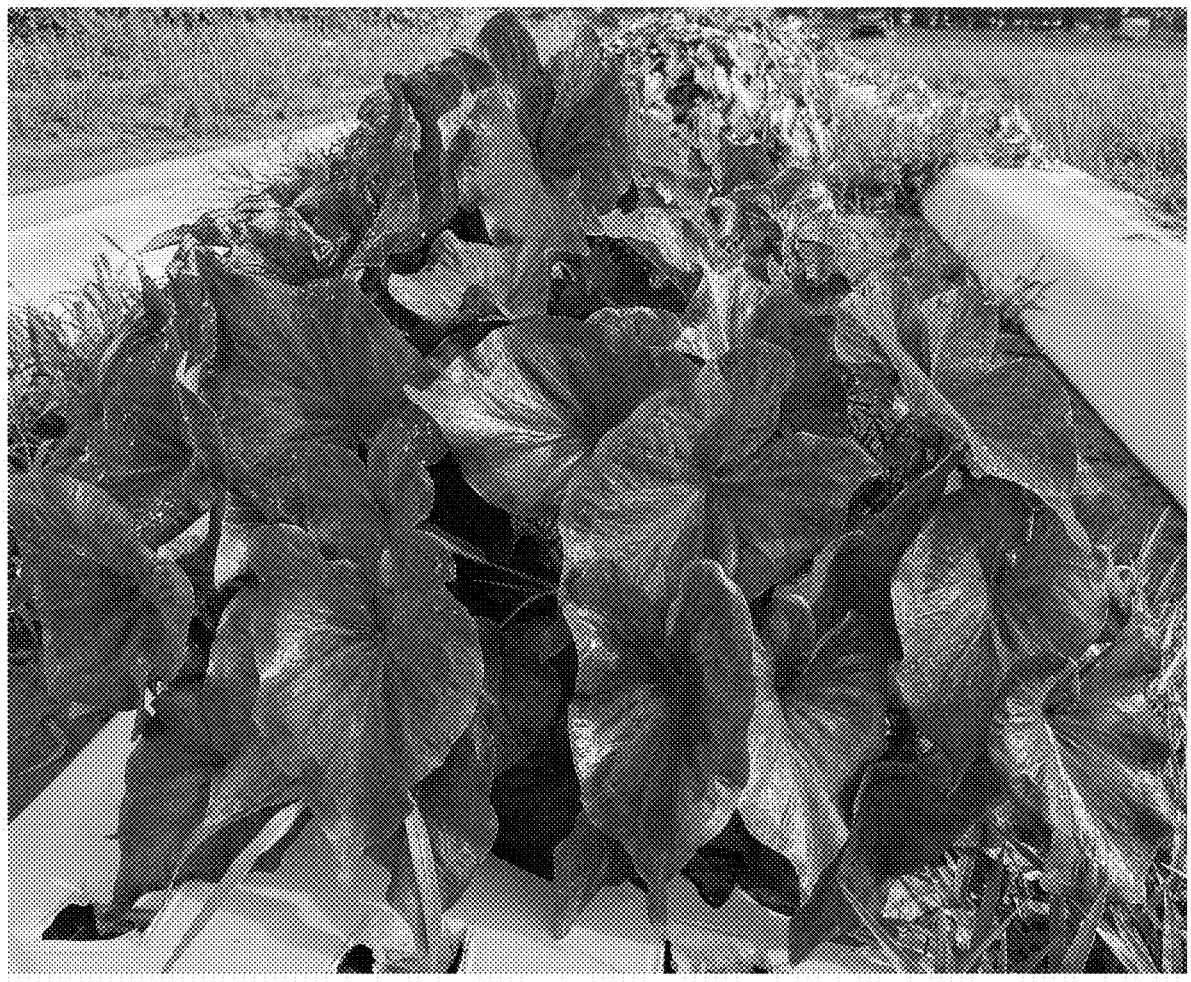
FIG. 5 shows a side perspective view of plants of 'UF-15-30' grown in an outdoor nursery in Wimauma, Florida.

In the following description, color references are made to The Royal Horticultural Society (R.H.S.) Colour Chart, 1986 Edition, except where general terms of ordinary dictionary significance are used.

Description of Growing Conditions

The aforementioned photographs and the following observations and measurements describe plants grown in 15-cm containers in Wimauma, Florida during the summer in a polypropylene-covered shade house and plants grown in an outdoor nursery in ground beds in Wimauma, Florida during the late summer. All plants were grown under conditions and practices that approximate those generally used in commercial *Caladium* production.

During the production of the plants, day temperatures ranged from about 26° C. to 35° C., night temperatures ranged from about 18° C. to 26° C. and light levels ranged from 2400 to 3840 foot-candles in the greenhouse to 8300 foot-candles for plants grown in the outdoor nursery. Plants grown in the greenhouse were 3 months old from tubers when the photographs and the detailed description were taken. Plants grown in the outdoor nursery were about 4 months old from tubers when the photographs and the detailed description were taken.

Botanical Description

Botanical classification:

*Family.*—Araceae.

*Botanical name.*—*Caladium* x *hortulanum.*

*Common name.*—*Caladium* or *Caladium.*

*Cultivar.*—'UF-15-30'.

Parentage:

*Female or seed parent.*—*Caladium* x *hortulanum* cultivar 'Florida Sweetheart' (expired U.S. Plant Pat. No. 8,526).

*Male or pollen parent.*—*Caladium* x *hortulanum* cultivar 'UF-67' (unpatented).

Propagation:

*Type.*—By tubers and by tuber divisions.

*Time to initiate roots, summer.*—About seven to ten days at 32° C.

*Time to initiate roots, winter.*—About two to three weeks at 24° C.

Tuber description:

*Number of buds per tuber* (*greenhouse-grown plants*).—About 6 to 10 actively growing buds/shoots.

*Number of buds per tuber* (*outdoor nursery-grown plants*).—About 4 to 6 actively growing buds/shoots.

*Height.*—4.0 cm.

*Diameter.*—3.7 cm.

*Texture.*—Thick, starchy, and hairy with fine dried roots.

*Color.*—Epidermis: 200D (brown). Interior: 15D (yellow-orange).

Root description: Dense, thick, and white fleshy roots.

Plant description:

*Type.*—Herbaceous perennial.

*Growth habit.*—Moderately vigorous, dense growth habit with an abundance of leaves, suitable for growing in 10 to 25-cm sized containers.

*Leaf petioles.*—Arising from tubers, mostly upright, curving outwardly with development.

*Plant height, from soil level to top of the leaf plane.*—Greenhouse grown plants: Average 29.2 cm. Outdoor nursery grown plants: Average 41.2 cm.

*Plant diameter or spread.*—Greenhouse-grown plants: Average 62.4 cm. Outdoor nursery grown plants: Average 60.8 cm.

Foliage description:

*Length.*—Greenhouse grown plants: Average 19.2 cm. Outdoor nursery grown plants: Average 22.3 cm.

*Width (flattened).*—Greenhouse grown plants: Average 12.8 cm. Outdoor nursery grown plants: Average 14.1 cm.

*Shape.*—Ovate to cordate.

*Apex.*—Acuminate.

*Base.*—Cordate.

*Margin.*—Entire.

*Texture.*—Upper surface: Smooth, glabrous. Lower surface: Smooth, glabrous; glaucous.

*Venation pattern.*—Pinnate.

*Color, developing leaves (greenhouse grown plants).*—Upper surface: Center: Interveinal space closer to the veins is 63B (red-purple) with pockets of 135A (green) also towards the margin of the leaf. Borders and margins: Margins are 147A (yellow-green) with a margin width up to 13.2 mm, and the border has a thin line of 58A (red-purple) on the extreme edge between upper and lower leaf surface. Basal notch: 58A (red-purple). Venation: Mid rib: 58A (red-purple). Primary veins: 60A (red-purple). Lower surface: Center: Interveinal space is 60C (red-purple) with pockets of 137C (green). Border and margins: 137C (green) with a margin width up to 12.8 mm and mottled section up to 28.0 mm towards the center of the leaf. Venation (midrib and primary veins): 193B (greyed-green) with streaks of 61A (red-purple).

*Color, fully expanded leaves (greenhouse grown plants).*—Upper surface: Center: Interveinal space closer to the veins is 59A or 60A (red-purple) with pockets of 135A or 136A (green). Borders and margins: 135C and 137B (green) with a margin width up to 17.1 mm and mottled area up to 34.2 mm towards the center of the leaf, and the border has a thin line of 61A (red-purple) on the extreme edge between the upper and lower leaf surface. Basal notch: 61A (red-purple). Venation: Mid rib: 137C or 138C (green). Primary veins: 63A (red-purple), 148D (yellow-green), and 138D (green). Lower surface: Center: Interveinal space is 64A or 72A (red-purple) with pockets 137D or 147C (green). Border and margins: 137C (green) with a margin width up to 21.3 mm. Venation: Mid rib: 137C or 138C (green). Primary veins: 138D (green), 148D (yellow-green) and streaked with 63A (red-purple).

*Color, developing leaves (outdoor nursery grown plants).*—Upper surface: Center: Interveinal space closer to the veins is 61A (red-purple) or 45A (red) with pockets of 131A (green) and 131A (green) towards the margin of the leaf. Border and margins: 135A (green) with a margin width up to 9.0 mm, and the border has a thin line of 59A to 59B (red-purple) on the extreme edge between upper and lower leaf surface. Venation (both the midrib and primary veins): 46A (red). Lower surface: Center: Interveinal space closer to the veins is 53B (red) with mottled areas of 138B (green) towards the edge. Border and margins: 147B (yellow-green) with a margin width up to 12.7 mm and mottled areas up to 34.1 mm towards the center of the leaf. Venation: Midrib: 156A (greyed-white), 157A (green-white) with streaks of 179A (greyed-red). Primary veins: 191A to 191B (greyed-green).

*Color, fully expanded leaves (outdoor nursery grown plants).*—Upper surface: Center: Interveinal space closer to the veins is 46A (red) with a few pockets and mottled areas of 131B and 132A (green) towards the margin. Border and margins: 135A and 137A (green) with a margin width up to 13.5 mm, and the border has a thin line of 59A to 59B (red-purple) on the extreme edge between the upper and lower leaf surface. Venation: Midrib: 46A (red). Primary veins: 46A (red) and 59B (red-purple). Lower surface: Center: Interveinal space closer to the veins is 59C and 60B (red-purple). Border and margins: 191A (greyed-green) with a margin width up to 19.2 mm and mottled areas up to 70.8 mm towards the center of the leaf. Venation: Midrib: 156A and 156B (greyed-white) and 157A (green-white) with streaks of 179A (greyed-red). Primary veins: 191A and 191B (grey-green).

*Petiole.*—Aspect: Mostly erect, curving outwardly with development. Length: Greenhouse grown plants: 27.0 cm. Outdoor nursery grown plants: 35.9 cm. Diameter, distal: Greenhouse grown plants: 3.3 mm. Outdoor nursery grown plants: 3.7 mm. Diameter, proximal: Greenhouse grown plants: 5.5 mm. Outdoor nursery grown plants: 6.5 mm. Color: Greenhouse grown plants: 195D (greyed-green) or 165C (greyed-orange), variably streaked with 200A (brown). Outdoor nursery grown plants: 159A (orange-white), 62D (red-purple) variably streaked with 200A (brown). Wing length: Greenhouse grown plants: Average 5.4 cm. Outdoor nursery grown plants: 6.0 cm. Wing diameter: Greenhouse grown plants: 7.0 mm. Outdoor nursery grown plants: 9.9 mm. Wing color: Greenhouse grown plants: 201D (grey), streaked with 202A (black) and 200A (brown). Outdoor nursery grown plants: 65D (red-purple) or 75D (purple), streaked 200A (brown).

Inflorescence description: Inflorescences have not been observed on plants of 'UF-15-30' grown in the field or in the greenhouse.

Disease and pest resistance: Disease and pest resistance have not been observed on plants of 'UF-15-30' grown in the field or in the greenhouse.

Sunburn resistance: 'UF-15-30' has been observed to be more tolerant to sunburns in open field grown plants than the *Caladium* cultivar 'Florida Sweetheart'.

Tuber Yield Potential

'UF-15-30' was also evaluated for tuber production and plant performance at the Wimauma, Florida in 2018 and 2020 and compared to plants of several other lance or strap-leaved cultivars including 'Fairytale Princess' (expired U.S. Plant Pat. No. 25,612), 'Red Hot' (expired U.S. Plant Pat. No. 25,598), 'Sizzle' (U.S. Plant Pat. No. 26,591), 'Florida Red Ruffles' (expired U.S. Plant Pat. No. 13,136), and 'Florida Sweetheart' (expired U.S. Plant Pat. No. 8,526). The soil was an EauGallie fine sand with approximately 1% organic matter and a pH of 6.2. *Caladium* plants were grown in the open field using a plastic mulched, raised bed system. Field plots were organized in a randomized complete block design consisting of three replications. Each plot was 1.2 $m^2$ and contained 30 *Caladium* propagules.

In the 2018 season, ground beds (81 cm wide, 20 cm high) were fumigated on February 13 with Pic-Clor 60 brand soil fumigant (39.0% 1,3-dichloropropene, 59.6% chloropicrin) at 448 $kg \cdot ha^{-1}$ and Prowl® H20 brand herbicide. *Caladium* seed tubers were treated in hot water (50° C.) for 30 minutes. Seed tuber pieces were dusted with RootShield® Plus WP brand fungicide and planted manually on April 27 with approximately 25.4 cm between-row spacing and approximately 15.2 cm in-row spacing. Fifty pounds of granular nitrogen (50 N) per acre was incorporated into the soil prior to bedding. Two drip tapes were buried under the plastic mulch along the raised beds, which provided the irrigation water and fertilization. Fertigation began on May 29, injecting a commercial liquid fertilizer (5N-0.87P-6.64K) at the rate of 0.454 kg of nitrogen an acre a day, and stopped on October 31. New crop tubers were dug and washed on December 17 and air-dried for approximately 50 days inside a greenhouse. Dried tubers from each experimental field plot were weighed, graded, and counted on Feb. 6, 2019.

For the 2019 evaluation, beds were fumigated on February 24 with Pic-Clor 60 brand soil fumigant at 448 $kg \cdot ha^{-1}$. *Caladium* seed pieces were planted on April 4. Fifty pounds of granular nitrogen (50 N) per acre was incorporated into the soil prior to bedding. Fertigation began on June 1 by injecting a commercial liquid fertilizer (5N-0.87P-6.64K) at 0.454 kg of nitrogen an acre a day. The fertilization rate was increased to 0.908 kg of nitrogen an acre a day on July 24 and ended on October 31. Tubers were dug and washed on December 9 and dried in the greenhouse for approximately 45 days.

In the 2020 season, ground beds were fumigated on February 12 with Pic-Clor 60 brand soil fumigant at 448 $kg \cdot ha^{-1}$. *Caladium* seed tubers were treated in hot water (50° C.) for 30 minutes. Seed tuber pieces were dusted with RootShield® Plus WP brand fungicide and planted manually on April 15 with the same in-row and between-row spacing as in 2018. Two drip tapes were buried under the plastic mulch along the raised beds to provide the irrigation water and fertilization. Fertigation began on May 28, injecting a commercial liquid fertilizer (5N-0.87P-6.64K) at the rate of 0.454 kg of nitrogen an acre a day, and ended on October 30. Tubers were dug and washed on December 1 and 2, dried in the greenhouse for approximately 63 days, and weighed, graded, and counted on Feb. 3, 2021.

In 2018, 'UF-15-30' produced significantly larger and more tubers than 'Fairytale Princess' or 'Red Hot'. In 2020, 'UF-15-30' was comparable to 'Florida Red Ruffles', 'Florida Sweetheart', and 'Sizzle' in tuber weight, marketable tubers, and production index (Table 1).

TABLE 1

Tuber weight, marketable number, production index, and grade distribution of 'UF-15-30' and commercial caladium cultivars (checks) in replicated experimental field plots in 2018 and 2020 in Wimauma, Florida. Values presented are means of three plots with 30 propagules planted in a plot of 1.2 m2.

| | Tuber | | | Tuber grade distribution (%) | | |
|---|---|---|---|---|---|---|
| | Weight | Market-able | Prod-uction | | | |
| | (kg) | (no.) | index | Jumbo | No. 1 | No. 2 |
| Cultivar | 2018 | | | | | |
| 'UF-15-30' | 2.10 a | 53.3 a | 106 a | 7.0 a | 53.1 a | 38.5 b |
| 'Fairytale Princess' | 0.12 b | 8.3 b | 10 b | 0 b | 0 b | 100.0 a |
| 'Red Hot' | 0.16 b | 6.7 b | 12 b | 0 b | 21.5 b | 78.5 a |
| P value | .0014 | .0005 | .0010 | .0347 | .0029 | .0031 |
| | 2020 | | | | | |
| 'UF-15-30 | 1.63 | 57.0 | 87 ab | 4.3 | 21.7 | 74.0 a |
| 'Sizzle' | 2.14 | 67.3 | 107 a | 3.5 | 28.7 | 67.3 a |
| 'Florida Red Ruffles' | 1.57 | 45.0 | 78 b | 9.7 | 31.0 | 59.3 b |
| 'Florida Sweetheart' | 1.86 | 50.0 | 82 b | 1.3 | 26.9 | 71.8 a |
| P value | .0758 | .3229 | .0155 | .2041 | .1506 | .0018 |

Additional Plant Comparisons

'UF-15-30' was evaluated for plant growth, leaf color display, sunburn tolerance, and leaf health in the same field plots that were used for evaluating tuber production potential. A scale of 1 to 5 was used for rating plant growth, with 1 being very poor (few leaves and lack of vigor) and 5 being excellent (full plants, numerous leaves). A scale of 1 to 5 was used for rating leaf color display, with 1 being very poor (dull or bleached, lack of color display) and 5 being excellent (bright). Sunburn tolerance was evaluated on a scale of 1 to 5, with 1 being very susceptible to sunburn (leaves having numerous sun-damaged areas or holes) and 5 being resistant to sunburn (no visible sun-damaged areas). Leaf health was evaluated on a scale of 1 to 5, with 1 being numerous diseased spots and completely unsightly and 5 being healthy and free of visible leaf spot disease.

In both years, 'UF-15-30' received higher leaf color scores than 'Florida Sweetheart' in five out of seven evaluations. 'UF-15-30' showed excellent sunburn tolerance in both 2019 and 2020, with a score of 3.3 to 4.5 (Table 2). These scores were higher than the scores 'Florida Sweetheart' received (2.0 to 4.2).

TABLE 2

Plant growth, leaf color, sunburn tolerance, and leaf health ratings of 'UF-15-30' and commercial caladium cultivars (checks) grown from 2.5-cm tuber propagules in ground beds in full sun in Wimauma, FL. Rating values are means of three plots based on whole plot evaluation in each evaluation.

| | Plant Growth Ratings 2019 | | |
|---|---|---|---|
| Cultivars | July | August | September |
| 'UF-15-30' | 2.8 | 3.5 | 1.5 |
| 'Fairy-tale Princess' | 2.3 | 2.8 | 2.0 |
| 'Florida Red Ruffles' | — | — | — |
| 'Florida Sweet-heart' | 2.8 | 3.0 | 1.7 |
| Sizzle | — | — | — |
| p value | .5289 | .4768 | .5487 |

| | Plant Growth Ratings 2020 | | | |
|---|---|---|---|---|
| Cultivars | July | August | September | October |
| 'UF-15-30' | 3.0 | 3.2 ab | 4.0 | 3.1 |
| 'Fairy-tale Princess' | — | — | — | — |
| 'Florida Red Ruffles' | 2.2 | 2.3 b | 4.3 | 3.3 |
| 'Florida Sweet-heart' | 2.3 | 2.3 b | 3.7 | 2.4 |
| Sizzle | 3.2 | 3.7 a | 4.8 | 3.1 |
| p value | .1188 | .0038 | .2579 | .1097 |

| | Sunburn Tolerance Rating 2019 | | |
|---|---|---|---|
| Cultivars | July | August | September |
| 'UF-15-30' | 4.0 | 4.5 a | 3.3 a |
| 'Fairy-tale Princess' | 3.7 | 4.2 a | 3.3 a |
| 'Florida Red Ruffles' | — | — | — |
| 'Florida Sweet-heart' | 4.2 | 3.8 b | 2.0 b |
| 'Sizzle' | — | — | — |
| p value | .4444 | .0400 | .0123 |

| | Sunburn Tolerance Rating 2020 | | | |
|---|---|---|---|---|
| Cultivars | July | August | September | October |
| 'UF-15-30' | 4.5 | 4.3 a | 3.5 ab | 3.3 ab |
| 'Fairy-tale Princess' | — | — | — | — |
| 'Florida Red Ruffles' | 4.5 | 4.5 a | 4.0 a | 4.2 a |
| 'Florida Sweet-heart' | 3.5 | 3.8 b | 3.0 b | 2.5 b |
| 'Sizzle' | 4.3 | 4.5 a | 4.0 a | 4.2 a |
| p value | .1170 | .0079 | .0075 | .0325 |

TABLE 2-continued

Plant growth, leaf color, sunburn tolerance, and leaf health ratings of 'UF-15-30' and commercial caladium cultivars (checks) grown from 2.5-cm tuber propagules in ground beds in full sun in Wimauma, FL. Rating values are means of three plots based on whole plot evaluation in each evaluation.

| | Leaf Color Rating 2019 | | |
|---|---|---|---|
| Cultivars | July | August | September |
| 'UF-15-30' | 4.3 a | 4.5 a | 2.5 a |
| 'Fairy-tale Princess' | 4.0 a | 4.0 ab | 3.0 a |
| 'Florida Red Ruffles' | — | — | — |
| 'Florida Sweet-heart' | 3.0 b | 3.5 b | 1.8 b |
| 'Sizzle' | — | — | — |
| p value | .0178 | .0331 | .0316 |

| | Leaf Color Rating 2020 | | | |
|---|---|---|---|---|
| Cultivars | July | August | September | October |
| 'UF-15-30' | 3.8 | 3.8 a | 4.0 a | 3.5 |
| 'Fairy-tale Princess' | — | — | — | — |
| 'Florida Red Ruffles' | 3.7 | 3.5 ab | 4.0 a | 3.8 |
| 'Florida Sweet-heart' | 3.3 | 3.2 b | 2.0 b | 2.8 |
| 'Sizzle' | 3.7 | 4.0 a | 3.3 ab | 3.8 |
| p value | .4547 | .0063 | .0161 | .0541 |

| | Leaf Health Rating 2019 | |
|---|---|---|
| Cultivars | August | September |
| 'UF-15-30' | 4.3 | 4.2 |
| 'Fairy-tale Princess' | 4.3 | 4.0 |
| 'Florida Red Ruffles' | — | — |
| 'Florida Sweet-heart' | 4.2 | 3.7 |
| 'Sizzle' | — | — |
| p value | .7901 | .2844 |

| | Leaf Health Rating 2020 | | | |
|---|---|---|---|---|
| Cultivars | July | August | September | October |
| 'UF-15-30' | 4.5 | 4.2 | 3.7 | 3.7 |

TABLE 2-continued

Plant growth, leaf color, sunburn tolerance, and leaf health ratings of 'UF-15-30' and commercial caladium cultivars (checks) grown from 2.5-cm tuber propagules in ground beds in full sun in Wimauma, FL. Rating values are means of three plots based on whole plot evaluation in each evaluation.

| | | | | |
|---|---|---|---|---|
| 'Fairy-tale Princess' | — | — | — | — |
| 'Florida Red Ruffles' | 4.5 | 4.5 | 3.8 | 4.2 |
| 'Florida Sweet-heart' | 4.5 | 4.0 | 4.0 | 3.8 |
| 'Sizzle' | 4.5 | 4.3 | 3.7 | 4.3 |
| p value | | .3942 | .7091 | .2010 |

Container Trials

'UF-15-30' was also evaluated and compared to 'Florida Sweetheart' for suitability for container plant production. The evaluation was conducted in 2022 by forcing tubers in 12.7-cm containers (diameter). Number 1-sized tubers (intact and de-eyed) were planted on Mar. 11, 2022. The experiment was arranged in a randomized complete block design with eight replicates. Containerized *Caladium* plants were evaluated on May 31 and June 1 2022, approximately 11 weeks after planting the tubers. 'Florida Sweetheart' was included as a commercial check. In this evaluation and when planted intact without tuber de-eyeing, 'UF-15-30' had significantly more leaves than 'Florida Sweetheart' (24.9 vs. 15.6) (Table 3).

TABLE 3

Days to sprout, plant height and width, leaf number, length and width, number of blooms (inflorescences), and plant quality ratings of 'UF-15-30' and commercial caladium cultivar 'Florida Sweetheart' (check) grown in small containers. No. 1 tubers were planted in 12.7-cm containers (one tuber per container) and grown in a shaded glasshouse in Wimauma, FL in 2021. Values represent the means of six plants (replicates) produced from intact or de-eyed No. 1 (3.8 to 6.4 cm in diameter) tubers planted individually per container.

| | Days to Sprout | | Plant Height (cm) | |
|---|---|---|---|---|
| Cultivar | Intact | De-eye | Intact | De-eye |
| 'UF-15-30' | 44.4 | 40.3 | 19.9 | 18.5 |
| 'Florida Sweetheart' | 49.7 | 41.6 | 19.1 | 21.0 |
| P value | .2818 | .4218 | .6221 | .2621 |
| | **Leaf Length (cm)** | | **Leaf Width (cm)** | |
| | Intact | De-eye | Intact | De-eye |
| 'UF-15-30' | 17.2 | 14.7 | 12.3 | 10.0 |
| Florida Sweetheart | 17.5 | 16.4 | 13.3 | 11.2 |
| P value | .8276 | .2431 | .1857 | .2969 |
| | **Plant Width (cm)** | | **Leaves (no.)** | |
| Cultivar | Intact | De-eye | Intact | De-eye |
| 'UF-15-30' | 36.6 | 34.4 | 24.9 a | 32.1 |
| 'Florida Sweetheart' | 34.1 | 39.6 | 15.6 b | 24.3 |
| P value | .3538 | .0902 | .0161 | .1403 |
| | **Blooms (no.)** | | **Quality Rating[z]** | |
| | Intact | De-eye | Intact | De-eye |
| 'UF-15-30' | 0 | 0 | 2.5 | 3.1 |
| Florida Sweetheart | 0.1 | 0 | 2.0 | 3.1 |
| P value | .3559 | | .1249 | .9679 |

I claim:

1. A new and distinct cultivar of *Caladium* plant named 'UF-15-30' as illustrated and described herein.

* * * * *